United States Patent
Laubert et al.

(10) Patent No.: US 10,507,119 B2
(45) Date of Patent: Dec. 17, 2019

(54) SPINAL INTERBODY DEVICE, SYSTEM AND METHOD

(71) Applicant: AESCULAP IMPLANT SYSTEMS, LLC, Center Valley, PA (US)

(72) Inventors: Nikolay S. Laubert, Center Valley, PA (US); Dana C. Lemesh, Center Valley, PA (US); Carl Lauryssen, Center Valley, PA (US); Larry Khoo, Center Valley, PA (US); Scott L. Blumenthal, Center Valley, PA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 0 days.

(21) Appl. No.: 14/134,962

(22) Filed: Dec. 19, 2013

(65) Prior Publication Data

US 2015/0173915 A1    Jun. 25, 2015

(51) Int. Cl.
| | | |
|---|---|---|
| *A61F 2/44* | (2006.01) | |
| *A61F 2/46* | (2006.01) | |
| *A61F 2/28* | (2006.01) | |
| *A61F 2/30* | (2006.01) | |

(52) U.S. Cl.
CPC ............ *A61F 2/447* (2013.01); *A61F 2/4455* (2013.01); *A61F 2/4611* (2013.01); *A61F 2002/2835* (2013.01); *A61F 2002/30367* (2013.01); *A61F 2002/30774* (2013.01); *A61F 2002/30787* (2013.01); *A61F 2002/30841* (2013.01); *A61F 2002/30845* (2013.01); *A61F 2002/30904* (2013.01); *A61F 2002/4627* (2013.01); *A61F 2002/4629* (2013.01)

(58) Field of Classification Search
CPC .. A61F 2002/30841; A61F 2002/30845; A61F 2002/448; A61F 2/442; A61F 2/445; A61F 2/447; A61F 2/4611; A61F 2/44
See application file for complete search history.

(56) References Cited

U.S. PATENT DOCUMENTS

| | | | |
|---|---|---|---|
| 5,531,554 A | 7/1996 | Jean-Francois et al. | |
| 6,896,676 B2 * | 5/2005 | Zubok et al. | 606/914 |
| 7,637,950 B2 * | 12/2009 | Baccelli et al. | 623/17.11 |
| 7,918,891 B1 * | 4/2011 | Curran et al. | 623/17.16 |

(Continued)

FOREIGN PATENT DOCUMENTS

EP    2 018 827 A1    1/2009

OTHER PUBLICATIONS

The extended European search report for the related European Patent Application No. 15181356.5 dated Feb. 2, 2016.

*Primary Examiner* — Kevin T Truong
*Assistant Examiner* — Marcela I Shirsat
(74) *Attorney, Agent, or Firm* — Kenealy Vaidya LLP (57) ABSTRACT

A spinal interbody device, system and method can include an interbody device configured to stabilize or otherwise support adjacent vertebrae. The interbody device can include a central opening and can be shaped as a trapezoid as viewed from a position on the central axis located above a superior or upper surface of the interbody device. In addition, the upper surface of the interbody device can include at least one keel or spike to facilitate locking of the interbody device with adjacent vertebrae. The at least one spike can be removable and can be adjustable relative to the superior or inferior surface(s) when installed.

32 Claims, 9 Drawing Sheets

(56) References Cited

U.S. PATENT DOCUMENTS

| | | | |
|---|---|---|---|
| 8,083,796 B1* | 12/2011 | Raiszadeh | A61F 2/442 623/17.11 |
| 9,005,293 B2 | 4/2015 | Moskowitz et al. | |
| 2003/0109928 A1* | 6/2003 | Pasquet et al. | 623/17.11 |
| 2004/0176844 A1* | 9/2004 | Zubok | A61F 2/442 623/17.15 |
| 2005/0027362 A1* | 2/2005 | Williams et al. | 623/17.11 |
| 2005/0043800 A1* | 2/2005 | Paul et al. | 623/17.15 |
| 2005/0049590 A1* | 3/2005 | Alleyne | A61F 2/442 623/17.11 |
| 2006/0276793 A1 | 12/2006 | Berry | |
| 2007/0270960 A1* | 11/2007 | Bonin, Jr. | A61F 2/442 623/17.11 |
| 2008/0183293 A1* | 7/2008 | Parry et al. | 623/17.11 |
| 2009/0076615 A1* | 3/2009 | Duggal | A61B 17/1604 623/17.16 |
| 2009/0210062 A1* | 8/2009 | Thalgott et al. | 623/17.16 |
| 2010/0217395 A1* | 8/2010 | Bertagnoli et al. | 623/17.16 |
| 2010/0305704 A1* | 12/2010 | Messerli et al. | 623/17.16 |
| 2011/0230971 A1* | 9/2011 | Donner et al. | 623/17.16 |
| 2012/0078373 A1 | 3/2012 | Gamache et al. | |
| 2013/0245767 A1* | 9/2013 | Lee et al. | 623/17.16 |

\* cited by examiner

SPINAL INTERBODY DEVICE, SYSTEM AND METHOD

BACKGROUND

1. Field

The presently disclosed subject matter relates generally to surgical instrumentation devices, systems, and related methods, and more specifically to a spinal interbody device, system and method for use in implanting an interbody device between adjacent (i.e., naturally adjacent, or separate and neighboring but not necessarily naturally adjacent) vertebrae.

2. Description of the Related Art

In order to stabilize two adjacent vertebrae of the spine, medical professionals will typically place a medical device, commonly referred to as an interbody device or cage, between adjacent target vertebrae. The cage will then be secured to the vertebrae using bone screws that traverse angled apertures in the cage to attach to upper and lower (inferior and superior) target vertebrae. Sometimes, a second component, typically referred to as a plate, is attached to both the cage and the upper and lower target vertebrae. The plate can be configured and used as disclosed in Applicant's co-pending U.S. patent application Ser. No. 13/944,545, the entire disclosure of which is incorporated herein by reference. Different insertion instruments have been used for each of the plate and the cage components.

Placement of the cage can be accomplished by a procedure known as anterior interbody fusion, which is a common technique for treating injured, diseased, or otherwise damaged vertebrae and/or disc(s) from an anterior approach. The anterior approach allows access to an interbody space with minimal damage to the posterior musculature, while allowing full decompression and/or stabilization of the diseased or damaged disc or vertebrae. The cage can include an interbody hollow or open area configured to receive bone graft or other bonding, grafting or regenerative material(s). The regenerative or bonding materials promote fusion of the adjacent vertebrae together.

SUMMARY

The conventional shape and configuration of a cage sometimes does not provide an adequate interface between adjacent vertebrae. In addition, connective forces that tend to keep a cage in place both immediately (during placement) and over time (during use) have sometimes been inadequate. Accordingly, it may be beneficial to provide a cage that is sized, shaped and/or configured such that installation can be accomplished with speed and accuracy while also providing consistent locking between the cage and adjacent vertebrae at a precise and relative position, both immediately during installation as well as over time during the life of the implant. In addition, a need has been uncovered for a device that has a low profile while providing the above-referenced features. In addition to the above, a need has been uncovered for a stand alone interbody device intended for use in the cervical region (C3 through C7) of the spine that provides the features of, for example, restoration of disc height, an ability to be fixed to vertebral bodies, and an ability to create opportunities for spinal fusion in cases of degenerative instability, post-discectomy syndrome and post-traumatic instability in the C3-C7 region.

According to one aspect of the disclosure, a spinal interbody system can include a interbody device configured to be placed between adjacent vertebrae of a spinal column, the interbody device including, an anterior surface, a posterior surface substantially opposed to the anterior surface, a lateral surface extending from the anterior surface to the posterior surface, a medial surface opposed to the lateral surface and extending from the anterior surface to the posterior surface, a superior surface connected to each of the anterior surface, posterior surface, lateral surface, and medial surface, an inferior surface opposed to the upper surface and connected to each of the anterior surface, posterior surface, lateral surface, and medial surface, an opening extending from the superior surface through the inferior surface, wherein an outermost periphery of the superior surface is shaped as a trapezoid.

According to another aspect of the disclosed subject matter, a spinal interbody device, can include a cage configured to be placed between adjacent vertebrae of a spinal column, the cage configured as a single unitary body consisting essentially of, an anterior surface, a posterior surface substantially opposed to the anterior surface, a lateral surface extending from the anterior surface to the posterior surface, a medial surface opposed to the lateral surface and extending from the anterior surface to the posterior surface, a superior surface connected to each of the anterior surface, posterior surface, lateral surface, and medial surface, an inferior surface opposed to the superior surface and connected to each of the anterior surface, posterior surface, lateral surface, and medial surface, an insertion structure located on at least one of the anterior surface, the medial surface, and the lateral surface, a first aperture extending from the anterior surface to the superior surface, a second aperture extending from the anterior surface to the inferior surface, an opening extending from the superior surface through the inferior surface, and at least one projection extending from at least one of the superior and inferior surface of the cage and configured to prevent movement of the cage relative to the adjacent vertebrae when implanted.

According to another aspect of the disclosed subject matter, a spinal interbody system can include an interbody device configured to be placed between adjacent vertebrae of a spinal column, and at least one keel. The interbody device can include an anterior surface, a posterior surface substantially opposed to the anterior surface, a lateral surface extending from the anterior surface to the posterior surface, a medial surface opposed to the lateral surface and extending from the anterior surface to the posterior surface, a superior surface connected to each of the anterior surface, posterior surface, lateral surface, and medial surface, an inferior surface opposed to the upper surface and connected to each of the anterior surface, posterior surface, lateral surface, and medial surface, and an opening located at a central portion of the interbody device. The at least one keel can have a longitudinal axis and a superior end located at one end of the longitudinal axis and an inferior end located at an opposite end of the longitudinal axis. The keel can extend from the superior surface through the inferior surface, such that the superior end extends out from the superior surface of the interbody device, and the inferior end extends out from the inferior surface of the interbody device. The at least one keel can include a blade that faces away from a central portion of the interbody device and away from the longitudinal axis of the keel (while extending along the longitudinal axis of the keel). A plurality of keels can be provided and the longitudinal axis of each keel can be substantially parallel with respect to the longitudinal axis of another keel.

BRIEF DESCRIPTION OF THE DRAWINGS

The disclosed subject matter of the present application will now be described in more detail with reference to exemplary embodiments of the apparatus, system, and method, given by way of example, and with reference to the accompanying drawings, in which.

DETAILED DESCRIPTION OF EXEMPLARY EMBODIMENTS

Figure 1:
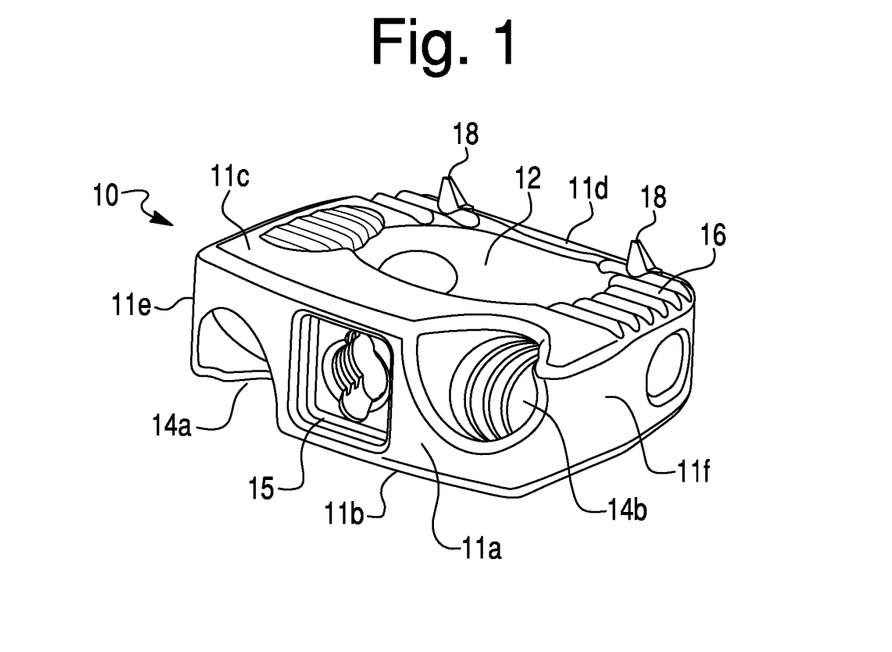
FIG. 1 is a perspective anterior view of an interbody device and system made in accordance with principles of the disclosed subject matter.

FIG. 1 is a perspective anterior view of one exemplary embodiment of an interbody device and system 10 made in accordance with principles of the disclosed subject matter. The interbody device 10 can be formed, for example, as a cage that can be molded, machined, printed, or otherwise formed as a single continuous structure. Alternatively, the interbody device 10 can comprise a plurality of separate structures that are attached, adhered, or otherwise assembled together. The interbody device 10 can be configured as a generally cuboid structure suitable for placement between adjacent vertebrae 81, 82 (see FIG. 7). In one embodiment, the interbody device 10 is intended to be used in the cervical region (C3 through C7) of the spine. The interbody device 10 can also be shaped so as to provide restoration of disc height when placed between the vertebrae 81, 82 and to generally mimic the spacing and structure of an intervertebral disk in this region.

The interbody device 10 can be configured for use in many different medical and surgical procedures, including to create opportunities for spinal fusion in cases of degenerative instability, post-discectomy syndrome, post-traumatic instability, and other diseases, injuries, or malformations in the spine, and particularly in the C3-C7 region.

Figure 2:
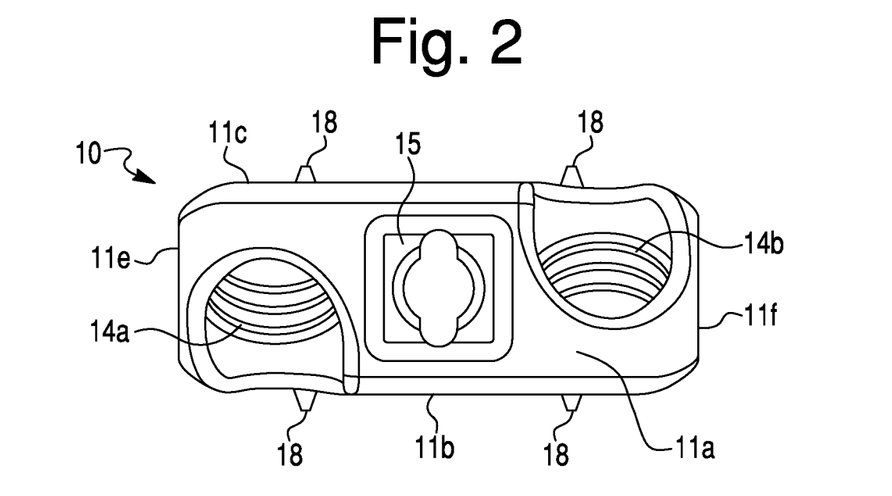
FIG. 2 is an anterior view of the interbody device and system of FIG. 1.

FIGS. 2-5 provide various views of the interbody device 10. The interbody device 10 can include an anterior or front surface 11a, an inferior or lower surface 11b, a superior or upper surface 11c opposed to the inferior surface 11b, a posterior or rear surface 11d opposed to the anterior surface 11a, a medial surface 11e, and a lateral surface 11f opposed to the medial surface 11e. Each of the surfaces 11a-11f can be immediately adjacent to each other to form the entire exterior facing surface of the interbody device 10. The anterior surface 11a can have an outermost periphery shaped as a substantial rectangle, and the posterior surface 11d can also have an outermost periphery shaped as a substantial rectangle, although smaller than the rectangle of the anterior surface 10a in this embodiment. The outermost periphery of each surface can be defined by the outermost extent of the surface when viewed along an axis that is substantially orthogonal to the surface that is being defined. For example, anterior surface 11a can be defined by the outermost periphery line as shown in FIG. 2.

Figure 3:
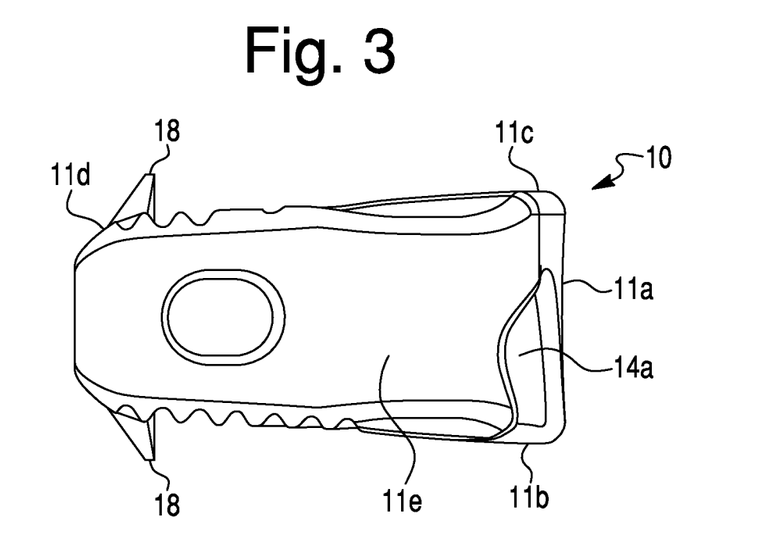
FIG. 3 is a medial view of the interbody device and system of FIG. 1.

FIG. 3 is a side view showing the medial surface 11e of the interbody device 10. In this embodiment, the medial surface 11e is shaped as a convex quadrilateral with at least one pair of parallel sides, for example, a trapezoid. Specifically, the outermost periphery of the medial surface 11e as shown or viewed from a distance that is orthogonal from the medial surface 11e can be formed substantially as an isosceles trapezoid.

Figure 4:
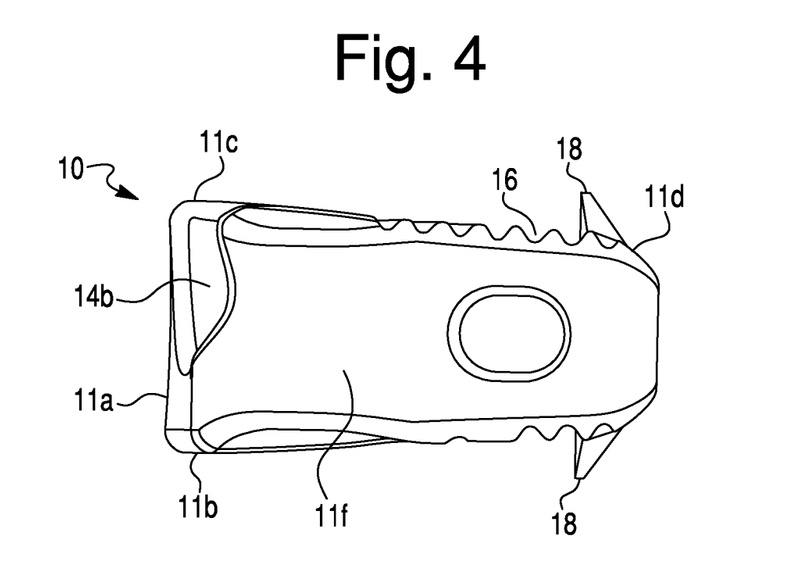
FIG. 4 is a lateral view of the interbody device and system of FIG. 1.

FIG. 4 is a side view showing the lateral surface 11f of the interbody device 10. The lateral surface 11f can be shaped as a trapezoid that is substantially identical to the trapezoidal shape of the medial lateral surface 11e, except for rotated 180 degrees about an axis extending orthogonally outward from the plane of FIG. 4 (i.e., about an axis that is orthogonal to both the central axis CA of opening 12 and central axis of attachment structure 15). Specifically, the outermost periphery of the lateral surface 11f as shown or viewed from a distance that is orthogonal from the lateral surface 11f in this embodiment can be formed substantially as an isosceles trapezoid.

As referenced above, the interbody device 10 can include an opening 12 that extends from the superior surface 11c to the inferior surface 11b. The opening 12 can include a central axis CA (see, for example, FIG. 7) that extends vertically through the entirety of the interbody device 10. The opening 12 can be configured to receive tissue, bone growth tissue or materials, ceramic materials, adhesives, regenerative materials, or other substances determined to be appropriate for a given procedure.

A keyway or attachment structure 15 can be located substantially at a center of the anterior surface 11a and configured for attachment to an installation tool 71 (see FIG. 7) and/or a plate (not shown) for facilitating connection between adjacent vertebrae. The attachment structure 15 can be shaped as a keyway or receptacle, or can be a projection, screw thread, key, or other connector structure.

The keyway or attachment structure 15 is shown as including a substantially (i.e., totally or almost totally) circular cylindrical aperture extending from the exterior anterior surface 11a of the interbody device 10 to an interior portion of the interbody device 10 located within opening 12. The attachment structure 15 can be located in a recess, such as a square recess as shown located in the anterior surface 11a of the interbody device 10. The recess can be configured to mate with a locking structure of the insertion tool 71 to allow for easy manipulation of the interbody device 10 when preparing the device 10 for implantation or when implanting the interbody device 10.

The attachment structure 15 can include at least one flange opening extending from a periphery of the cylindrical aperture. The flange opening can run along an interior face of the attachment structure 15 and parallel with the longitudinal or central axis of the cylindrical aperture. The cross-section shape of the flange opening as viewed from a longitudinal/central/symmetrical axis of the attachment structure 15 (as viewed in FIG. 2) can be shaped and dimensioned to match the shape and dimensions of a projection portion on insertion tool 71.

The flange opening(s) are shown as semi-circular lobes, but can be formed in many different shapes, sizes, dimensions and orientations. For example, the flange opening(s) can be rectangular, square, triangular, or other polygonal shape. In addition, the flange opening(s) can be curved in a semi-oval shape, non-symmetrical shape, symmetrical curved free form shape, or other shape. If more than one flange opening is located in the attachment structure 15, each of the flange openings can have the same or different general shape. Further, the flange opening(s) can be constructed such that it/they selectively allow different size or shape mating portions of the insertion instrument 71 to pass through. Of course, the attachment structure 15 can be a simple threaded opening with no flange opening, or other structure surrounding the threaded opening.

Figure 5:
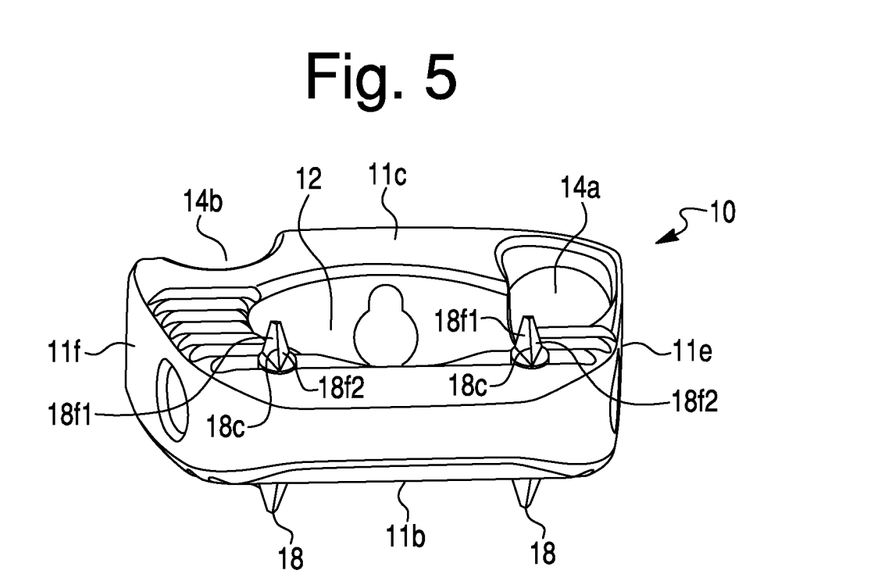
FIG. 5 is a perspective superior/posterior view of the interbody device and system of FIG. 1.

FIG. 5 is a perspective posterior view of the interbody device 10 which can include a main cage opening 12 designed to be filled with a bone regenerative material and/or biocompatible adhesive material that facilitates the fusing of the upper and lower vertebrae 81, 82, either immediately or over time, depending on surgical/medical treatment parameters and indications. The superior surface 11*c* of the interbody device 10 can include the main cage opening 12 that extends through to the inferior surface 11*b* of the interbody device 10. In addition, one or both of the superior surface 11*c* and inferior surface 11*b* can include at least one keel or locking projection 18. The keel or locking projection 18 can be used to assist frictional connection to vertebrae 81 and/or 82 during initial placement of the device as well as assist in long term prevention of migration of the interbody device 10 with respect to the vertebrae 81, 82 and enhance implant stability, especially under axial torsion loading.

The keel or locking projection(s) 18 can be formed as a spike shaped element that can be integral with the interbody device 10. Alternatively, the keel or projection(s) 18 can be structure(s) that are separately and selectively attached to the interbody device 10. For example, different shaped or sized projections 18 can be used or attached to the superior surface 11*c* and/or inferior surface 11*b* of the interbody device 10 depending on application and/or medical professional desire. The locking projection(s) 18 can also be located immediately adjacent the main cage opening 12 such that the interbody device 10 is prevented from movement relative to the adjacent vertebrae to which the interbody device 10 is attached. Thus, the interbody device 10 can promote stability between adjacent vertebrae and can also promote bone ingrowth into the interbody device 10 including within the main opening 12. If desired, the interbody device 10 can include knurls 16 in addition to the keel or projection(s) 18. The knurls 16 can be located on any of the surfaces 11*a*-11*f* to provide a higher frictional characteristic between that surface of the interbody device 10 and its intended adjacent structure, such as tissue, bone or vertebrae. Typically the locking projection(s) 18 are taller than knurls 16 (i.e., the projections 18 extend away from a surface of the cage or interbody device 10 further than do the knurls 16). However, it is contemplated that certain knurls 16 or portions of the knurls 16 could extend outward from a surface of the device 10 a further distance than do the projection(s) 18.

The knurls 16 can be configured as a series of grooves that extend upward and away from any of the surfaces 11*a*-11*f* of the interbody device 10. Alternatively, the knurls 16 can be configured as a plurality or matrix of discrete extensions, as a roughened surface, as a non-symmetrical or random series of extensions designed to either increase the coefficient of friction between the interbody device 10 and the adjacent tissue or object, or to increase the tissue repair and/or bone in growth into or adjacent the interbody device 10. Furthermore, the knurls 16 can be a separate structure that is attached to any of the surfaces 11*a*-11*f* (or within opening 12), such as a mesh, or ceramic bone ingrowth material, other bone or tissue regenerative material, etc. The projection(s) 18 can differ from the knurls 16 in that the projections can extend at least two times further from the superior surface 11*c* and/or inferior surface 11*b* than do the knurls 16. In addition, the projection(s) 18 can be configured such that, upon insertion between adjacent vertebrae, the compressive pressure of the vertebrae 81, 82 will cause the projection(s) 18 to make contact with and actually enter at least an outer bone surface of the vertebra. Depending on the configuration of the projection(s) 18, when the device 10 is implanted, the projection(s) 18 can extend into the periosteum and possibly even the compact bone of a vertebra. For example, the keel or projection(s) 18 can extend away from an outer surface of the device 10 a distance of 1 mm or 2 mm. Of course, this distance can vary significantly depending on the application and user preference. In addition, the height of each projection 18 can be equal to or can vary with respect to the height of other projection(s) 18.

The interbody device 10 can also include medial and lateral openings or apertures that extend from the medial surface 11*e* and lateral surface 11*f* of the interbody device 10 to the main cage opening 12. These openings/apertures can be designated for bone or other tissue in growth, can provide further anchor locations, or can be openings that simply reduce the overall weight of the device. Likewise, opening or apertures can be provided in any of the surfaces 11*a*-11*f* and extend either through the entire body of the interbody device 10 to another of the surfaces 11*a*-11*f* or through to the central opening 12 in the interbody device 10.

As shown in FIG. 5, a medial/left aperture 14*a* and a lateral/right aperture 14*b* can be provided in the anterior surface 11*a* of the interbody device 10. The apertures 14*a*, 14*b* can extend from the anterior surface 11*a* to the superior surface 11*c* and inferior surface 11*b* of the interbody device 10, respectively. The apertures 14*a*, 14*b* can also include a countersunk portion that allows a head of a screw 24*a*, 24*b* to fit neatly within each aperture 14*a*, 14*b* (i.e., with little or no portion of the screw 24*a*, 24*b* extending outside of a plane containing the anterior surface 11*a*). Thus, screw 24*a* can be inserted through left aperture 14*a* and into vertebra 81 and another screw 24*b* can be inserted through right aperture 14*b* and into vertebra 82 to lock the interbody device 10 with respect to vertebrae 81, 82. Although the apertures 14*a*, 14*b* are shown as countersunk and generally circular cylindrical apertures, it is contemplated that the apertures 14*a*, 14*b* can be configured as ovoid apertures, slots, polygonal apertures, non-symmetrical apertures or the like depending on the shape and type of bone attachment structure to be used with the interbody device 10. For example, a typical bone screw 24*a* having a rounded or tapered head could be used with the interbody device 10. However, different types of attachment heads could be used, and different types of attachment structures could be used, such as pins, barbs, rivets, trocars, cements, and other adhesive or attachment structures.

Figure 6:
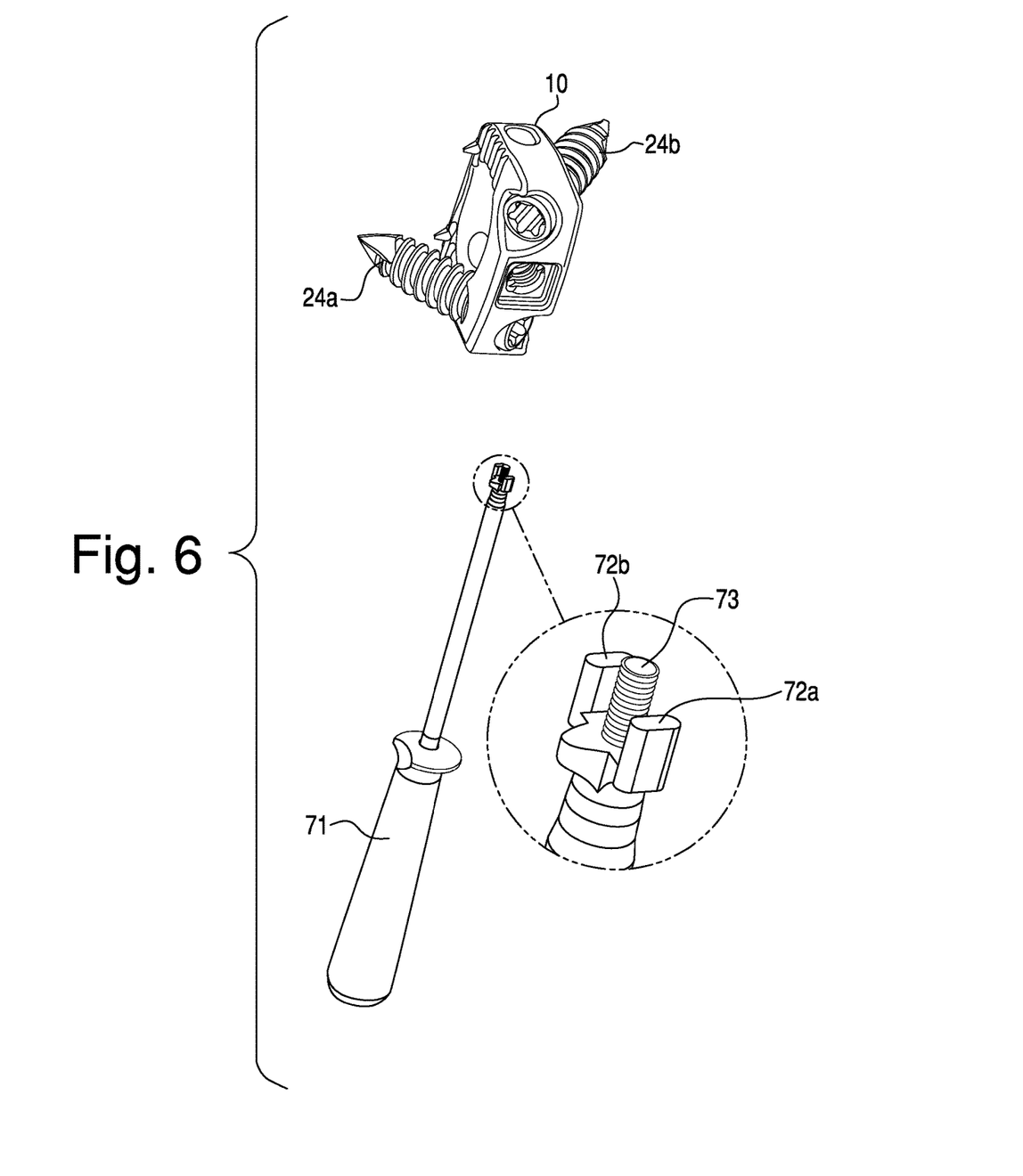
FIG. 6 is a perspective view of another interbody device and system made in accordance with principles of the disclosed subject matter.

FIG. 6 shows an interbody system in which installation tool 71 can be used in conjunction with movement of the interbody device 10, such as when placing the interbody device 10 in position relative to vertebrae 81, 82 (or relative to other interbody devices). The tool 71 can have a threaded end 73, such as M3 threads. In order to achieve attachment between the installation tool 71 and interbody device 10, the attachment structure 15 can include threads, such as M3 threads, that mate with threads on the installation tool 71. A recess, such as the square recess as shown, can be provided in the anterior surface 11a of the interbody device 10 such that the recess mates with similarly shaped projections 72a, 72b of the insertion tool 71 when the insertion tool threads are locked onto the threads of the cage. Thus, the recess will lock the tool 71 with the interbody device 10 such that no relative rotation can take place between the tool 71 and interbody device 10. When locked together in this manner, the insertion tool 71 can be used to extend the interbody 10 device through an incision/opening in a patient to deliver the interbody device 10 to a location between target vertebrae 81, 82. Alternatively, the insertion tool 71 can include connective elements different from the shown screw threads 73, such as but not limited to a button lock mechanism, rivet type connection, a frangible connection, a welded connection, etc. In addition, various other structures can be provided instead of locking projection 72a, b that can prevent rotation of the interbody device 10 relative to the insertion tool 71, such as but not limited to keyway projections and receptacles, adhesives, separate set screw or locking pin, non-symmetrically shaped attachment structures, ratcheting posts/receptacles, etc.

Figure 7:
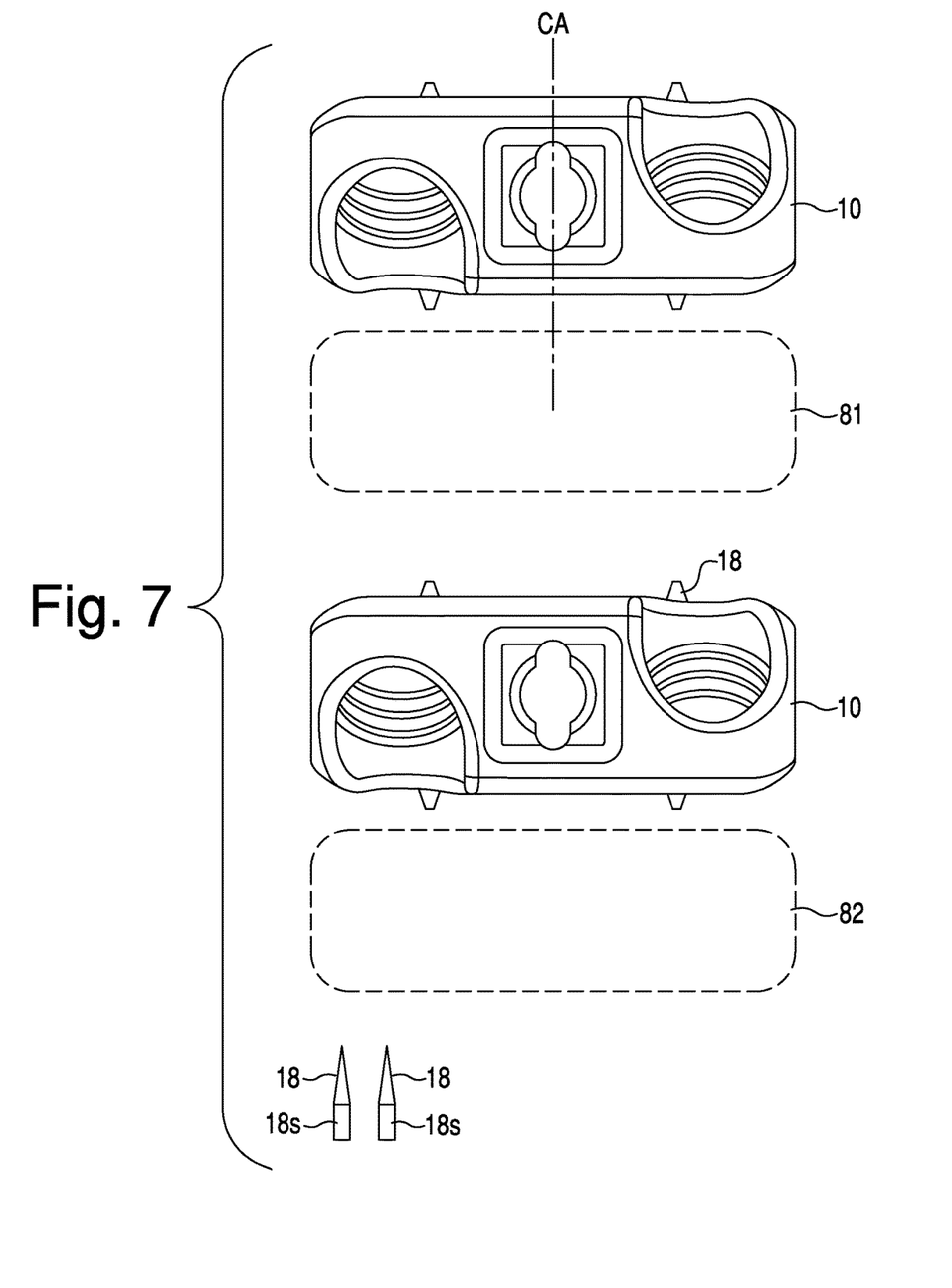
FIG. 7 is an anterior schematic view of another interbody device and system made in accordance with principles of the disclosed subject matter.
Figure 8:
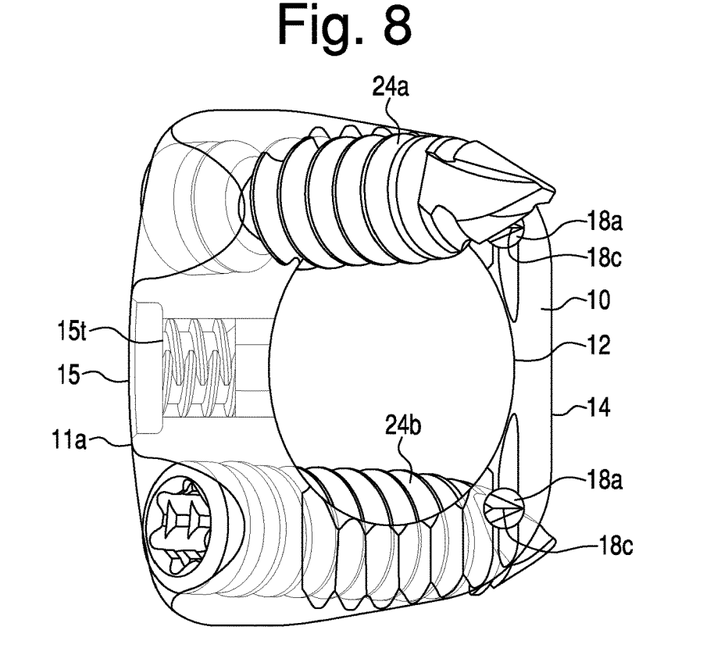
FIG. 8 is a partially transparent top or superior view of another embodiment of an interbody device and system made in accordance with principles of the disclosed subject matter.

FIG. 7 depicts an exemplary installation and method for attaching the interbody device 10 to adjacent vertebrae 81 and 82. In this embodiment, the system can include a plurality of interbody devices 10, each one stacked above the other such that the central axis of the opening 12 for each interbody device 10 is substantially aligned or co-linear. In addition, a plurality of different types of projections 18 can be provided in this embodiment. Specifically, each projection 18 can include a thread 18s located at a base thereof that can mate with inner threads located in the interbody device 10. Thus, if a longer (or differently shaped) projection(s) 18 is/are desired, a user can remove a first projection 18 and replace it with a second differently shaped projection 18. The shape of the projection(s) can vary greatly, from a pointed spike, to a rounded knub, to a spade shaped or barbed protrusion, etc. The shape can be determined by the particular application and/or the desire or preference of the user. In addition, although threads 18s are shown as the connection mechanism in the depicted embodiment, it should be understood that many other connective structures, methods or materials are contemplated for use with the disclosed subject matter. For example, the projection(s) 18 could be adhered to the superior or inferior surface(s) of the interbody device using various surgical cements or glues, such as polymethylmethacrylate, and other known surgical and medical device adhesives. Alternatively, magnetic force, welding, or simple friction fitting could be used for initial or final placement of the projection(s) 18. In addition, it is contemplated that the projection(s) could be movable relative to the interbody device 10 before during or after implantation of the interbody device. In the depicted example, the length that the projection(s) 18 extend away from either the superior surface 11c or inferior surface 11b can be determined by the amount of turns or rotations given to the projection(s) 18 when installing the threads 18s into a mating threaded aperture in the interbody device 10. Similarly, the amount of projection of each projection 18 can be determined by various other types of attachment structures, such as a ratcheted post and receptacle, etc. In a more complicated embodiment, the amount that the projection(s) 18 extend away from either the superior surface 11c or inferior surface 11b can be altered after the interbody device 10 is located between vertebrae 81, 82 by use of a linkage mechanism or cam mechanism that is operated from, for example, the anterior surface 11a to cause the projections to move outward or inward relative to the interbody device 10. Thus, the interbody device could be placed between adjacent vertebrae 81, 82 and only after correct placement is achieved would the projection(s) 18 be caused to extend from the superior surface 11c and/or inferior surface 11b to connect and lock into vertebrae 81, 82 respectively.

It should be noted that the keel or projection(s) 18 can serve several different functions. For example, projection(s) 18 can enhance implant stability, and can also facilitate radiologic identification and orientation of the interbody device 10 in a surgical space, such as between adjacent vertebrae 81, 82. With respect to the function of identification and orientation, the projection(s) 18 can be made from radio-opaque material(s) such that they serve as a posterior X-ray marker for the device and system 10. Thus, under X-ray, the keel or projection(s) 18 are visible while the interbody device 10 may be transparent.

With respect to the function of implant stability, a plurality of projections 18 can be provided and aligned with respect to each other (i.e., such that two projections 18 are opposed to each other along an imaginary linear axis). Such a configuration can provide enhanced implant stability, especially under axial torsion loading. This function can also be enhanced by providing two fixation points (i.e., two projections 18) at the superior and inferior implant surfaces, with each projection having an opposed projection extending in an opposite direction along a longitudinal axis. Each of the projections 18 can be considered to be a mini keel.

In one embodiment, the projections 18 can include a self-cutting blade 18c running between two faces 18/1 and 18/2 of the projection 18. The blade 18c can extend to a sharpened tip of the projection 18. The projection 18 can be self-cutting due to this sharp blade 18c (cutting edge) facing in an anterior direction. During implantation, a user such as a surgeon can deliver the interbody device 10 into the disk space without using additional instruments to prepare a path/channel for the keels or projections 18. Thus, less surgical steps are necessary.

In another embodiment, the interbody device 10 can be coated with a coating, such as Plasmapore$^{XP}$ (pure Titanium porous coating: titanium layer and a vacuum plasma spray coating) or one of the coatings disclosed and referenced in European Patent No. EP2548587 A1, which disclosure is hereby incorporated by reference. The coating may provide the following exemplary benefits: long term implant stability due to osteointegration, faster fusion, enhanced implant stability and migration resistance due to rough surface finish (high coefficient of friction), reduced fibrous tissue growth at the bone-implant interface, improved imaging properties.

FIGS. 8-12 depict another embodiment of an interbody device and system 10 made in accordance with principles of the disclosed subject matter. The interbody device 10 can be formed, for example, as a cage that can be molded, machined, printed, or otherwise formed as a single continuous structure. Alternatively, the interbody device 10 can comprise a plurality of separate structures that are attached, adhered, or otherwise assembled together. The interbody device 10 can be configured as a generally cuboid structure suitable for placement between adjacent vertebrae 81, 82.

The interbody device 10 can include an anterior or front surface 11a, an inferior or lower surface 11b, a superior or upper surface 11c opposed to the inferior surface 11b, a posterior or rear surface 11d opposed to the anterior surface 11a, a medial surface 11e, and a lateral surface 11f opposed to the medial surface 11e. Each of the surfaces 11a-11f can be immediately adjacent to each other to form the entire exterior facing surface of the interbody device 10. In general, the interbody device 10 can be shaped similar to that described above with respect to FIG. 1 and can include screws 24a and 24b for connecting to vertebrae or other tissue when implanted. Similar to the embodiment of FIG. 1, an opening 12 provided in the device 10 can be configured as a through hole, but can also be an interior pocket that is confined within the cage or interbody device 10, and can shaped in various manners.

The interbody device 10 can also include a keyway or attachment structure 15 that extends from the anterior surface 11a to opening 12 in the interbody device 10. The keyway 15 can include threads 151 for connection to an insertion tool, such as insertion tool 71 or other insertion or gripping/holding device.

Figure 9:
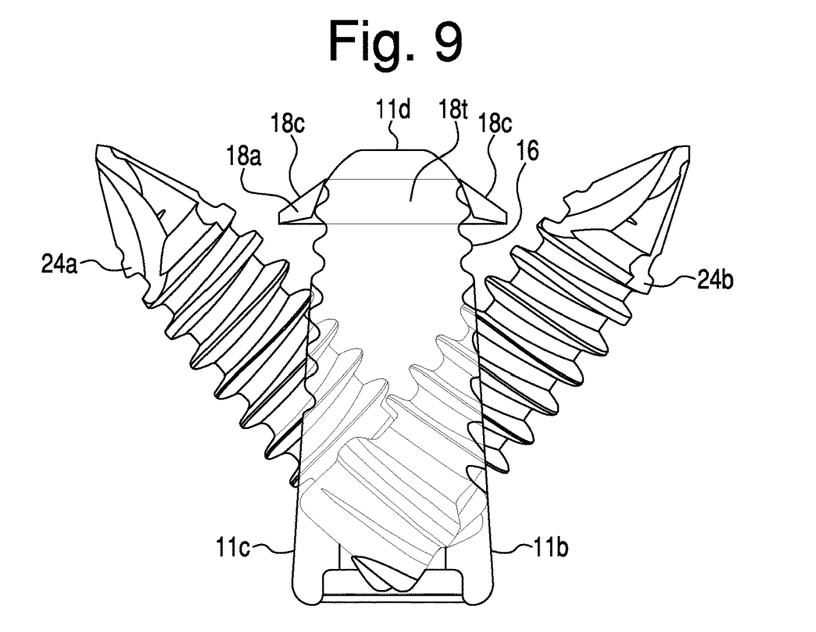
FIG. 9 is a partially transparent lateral or side view of the interbody device and system of FIG. 8.
Figure 10:
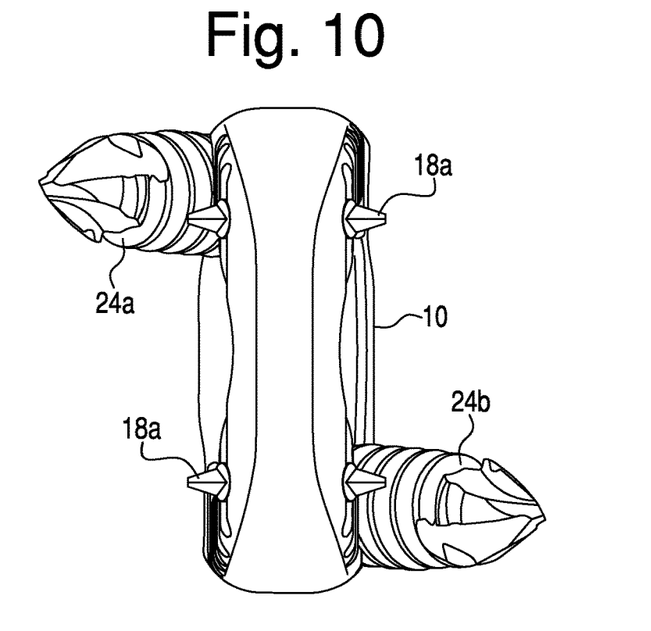
FIG. 10 is a posterior view of the interbody device and system of FIG. 8.

FIG. 9 depicts the keel or projections 18a as each being a single unitary and continuous structure that extends the entire distance through the interbody device 10, from the inferior surface 11b to the superior surface 11c. Each keel or projection 18a can be constructed from a single material and include a point and/or blade 18c at each opposing end of a longitudinal axis of the projection 18a. The keel or projection 18a can be press fit, welded, adhered, cemented, screwed, or otherwise attached into a mating opening in the interbody device 10. In particular, an intermediate portion 18t of each keel or projection 18a can be located within and connected or fixed to the interbody device 10. In one example, the intermediate portion 18t can be threaded such that the threads of the intermediate portion 18t mate with threads located along the opening in which the keel or projection 18a resides. When multiple keels or projections 18a are provided, each of the longitudinal axes of the projections 18a can be substantially parallel with respect to each other, and can be substantially perpendicular to one or both of the superior surface 11c and inferior surface 11b of the interbody device 10. As shown in FIG. 9, the outermost ends of the keel or projection 18a can extend away from the surfaces 11c and 11b. In addition, the longitudinal length of the keel or projection 18a is substantially equal to a height of the posterior-most portion of the interbody device 10 (the height defined horizontally in FIG. 9 from surface 11c to 11b at the bottom most portion of the interbody device 10).

Figure 11:
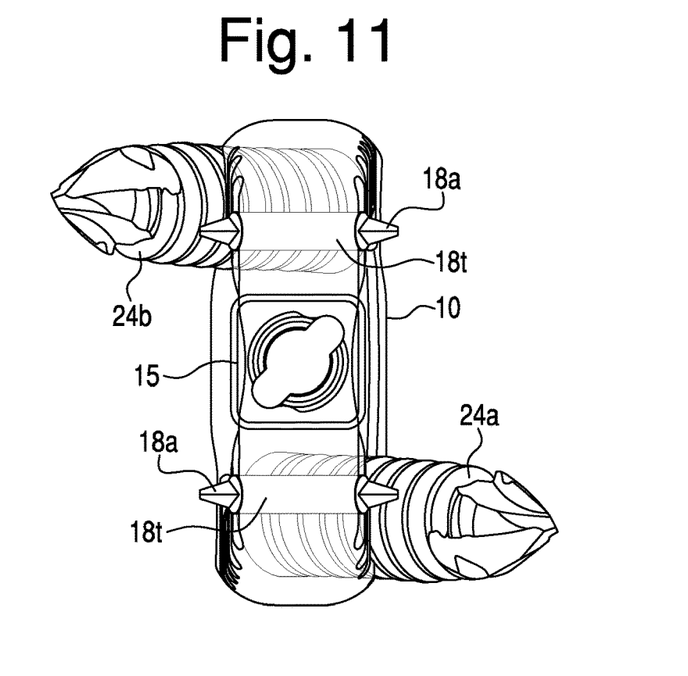
FIG. 11 is a partially transparent posterior view of the interbody device and system of FIG. 8.
Figure 12:
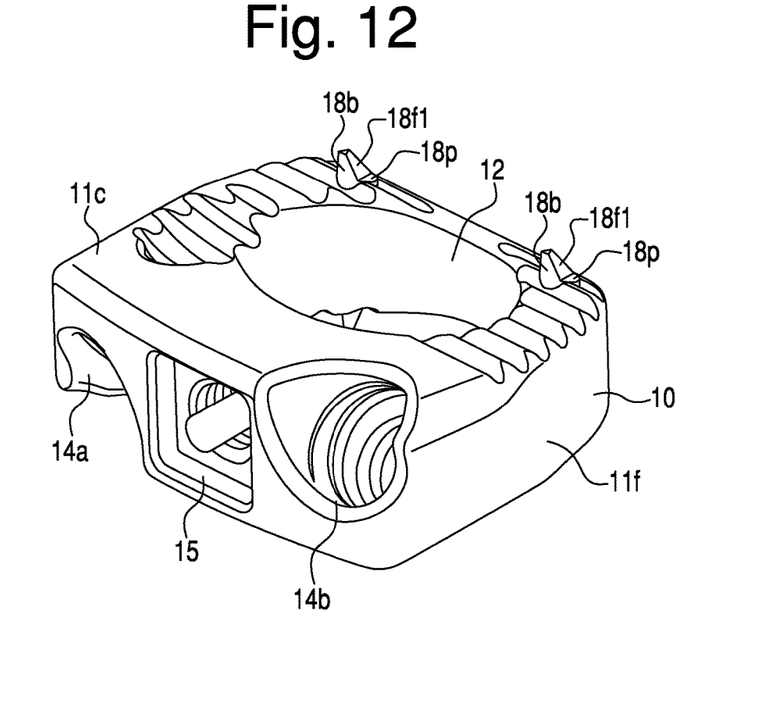
FIG. 12 is an anterior perspective view of a portion of the interbody device and system of FIG. 8.
Figure 13:
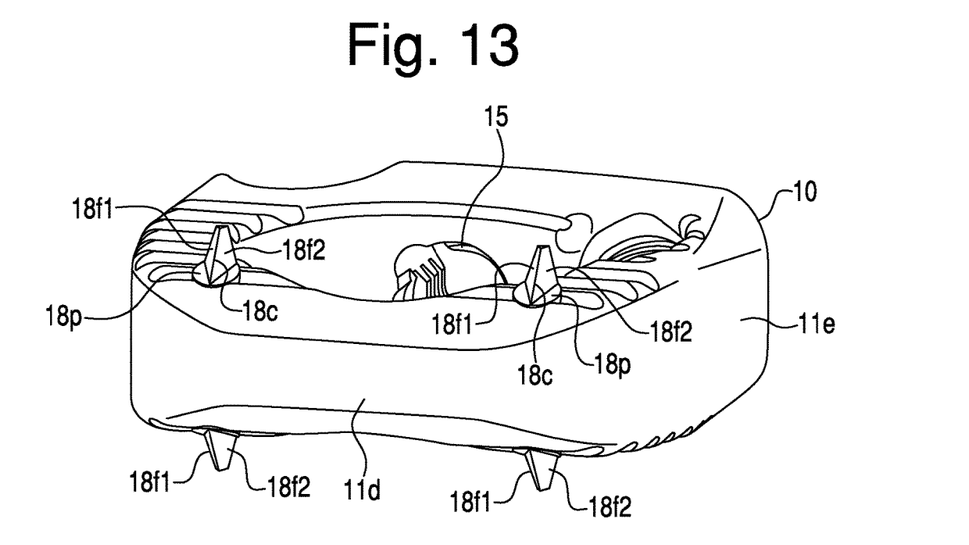
FIG. 13 is a posterior perspective view of the portion of the interbody device and system of FIG. 12.
Figure 14:
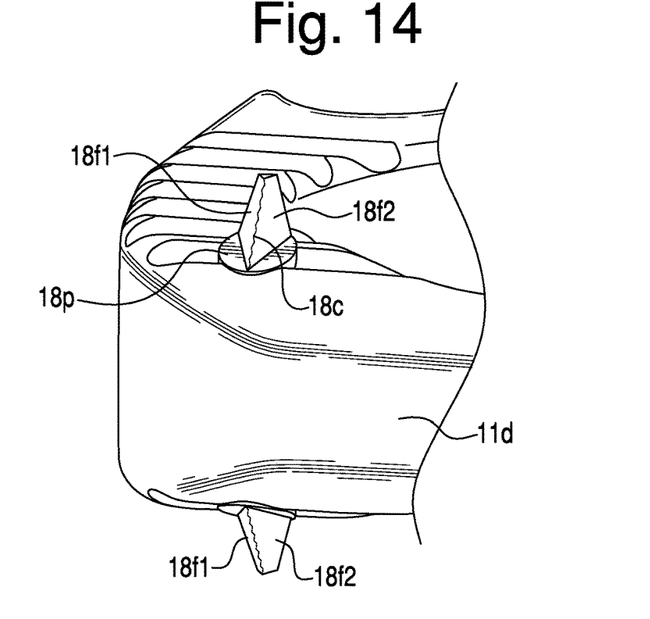
FIG. 14 is a close up view showing a portion of the interbody device and system of FIG. 13, including a blade having serrations.

FIGS. 11-13 show the keel or projection 18a as including a blade 18c defined between a first face 18/1 and a second face 18/2, which are located at opposing ends of the keel or projection 18a. The blade 18c can be configured to run along and substantially parallel with the longitudinal axis of the projection 18a. In addition, the blade 18c can be configured to face outward and away from a central portion of the interbody device 10 (e.g., away from opening 12 in the interbody device 10). More particularly, the blade 18c can be configured to face in a direction of implantation of the interbody device 10, such as in an anterior facing direction. The blade 18c can form an oblique angle with respect to either the superior surface 11b or inferior surface 11c such that the blade 18c forms a ramp that extends upward and away from either the superior surface 11b or inferior surface 11c as one moves from the posterior surface 11d side of the interbody device 10 to the anterior surface 11a side of the interbody device 10 along the superior or inferior surface 11b,c. Thus, the blade 18c forms a self-cutting device that can automatically cut into tissue during the implantation procedure when the interbody device 10 is slid or otherwise placed into position between, for example, vertebrae 81, 82. The blade 18c can include serrations (shown in FIG. 14) or other structures to assist in this self cutting function.

Figure 15:
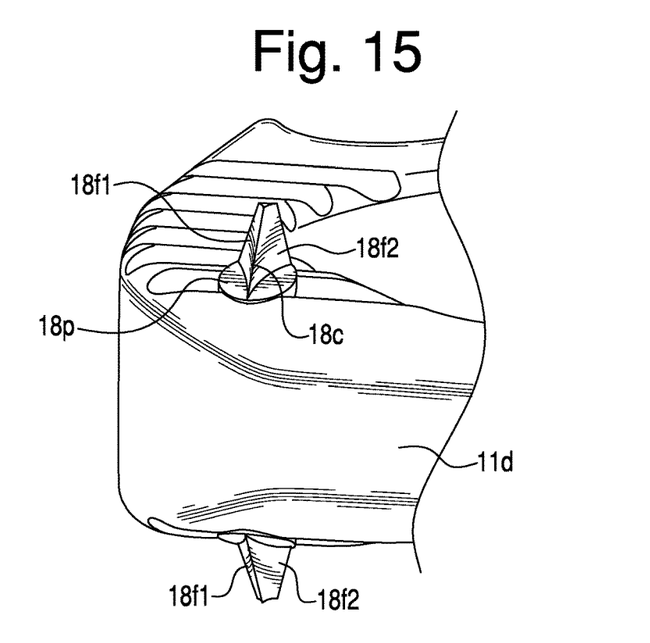
FIG. 15 is a close up view showing a portion of the interbody device and system of FIG. 13, including a blade having concave faces.

The faces 18/1 and 18/2 that form the blade 18c can be planar flat surfaces. However, these faces 18/1 and 18/2 can also be concave surfaces, as shown in FIG. 15, that might act similar to a snow plow device when pushed through tissue to spread the cut tissue and facilitate easy placement of the interbody device 10 during implantation. The faces 18/1 and 18/2 can all be similarly or differently shaped with respect to each other and with respect to separate keels or projections 18a. A rounded back surface 18b can be located opposite the blade 18c and faces 18/1 and 18/2. The rounded back 18b can extend from a location adjacent one of the superior surface 11b and inferior surface 11c to a pointed tip of the projection 18a. A ledge surface 18p can be formed in front of the faces 18/1 and 18/2 of the projection 18a and opposite the back surface 18b. The ledge surface 18p can be configured such that it is flush with a respective one of the superior surface 11b and inferior surface 11c when installed in the interbody device 10. The faces 18/1 and 18/2 can ramp upwardly from the ledge surface 18p to form the blade 18c between the faces 18/1 and 18/2. The blade 18c can extend from the ledge surface 18p to the point of projection 18a where the blade 18c terminates at a location joined with the back surface 18b. Thus, each of the surfaces 18/1, 1812 and 18b can be formed in a generally triangular shape with an apex of each triangle joined together to form a pointed end of the projection 18a.

While certain embodiments of the invention are described above, it should be understood that the invention can be embodied and configured in many different ways without departing from the spirit and scope of the invention. For example, the material from which the interbody device 10 is made can vary considerably, and can include stainless steel, titanium, aluminum, alloys, ceramics, carbon fiber, PEEK, plastics, bone, and other biocompatible and/or bone regenerative materials naturally occurring or man-made materials. Each of the structures can also be supplemented with bio-compatible and/or bone/tissue regenerative materials, such as meshes or platings that can be attached or formed on surfaces of the interbody device 10 or keels/projections 18, 18a. The interbody device 10 and keels or projections 18, 18a can be made from the same or different material depending on particular applications and desires of a user. The specific overall shape of the interbody device 10 and/or projections 18, 18a can also vary widely in accordance with patient needs or user preference. The shapes can also be predetermined for a specific patient through the use of pre-operative imaging and subsequent computer modeling of each of the interbody device 10 and keel or projection(s) 18, 18a.

With respect to the various methods that can be used to practice the presently disclosed subject matter, it is contemplated that the specific steps can be executed sequentially, but can also be executed simultaneously and/or in reverse or other orders. Other insertion tools could be used with the interbody device 10, including an insertion tool that does not require threads and matching threads for attachment and insertion of the various structures. For example, the insertion tool can be formed as a clamp or can include a rivet, cam, trocar, pin, or other locking structure for attaching to the interbody device 10.

The interbody device 10 depicted can be used for the cervical region of the spinal column. However, it is contemplated that the disclosed subject matter could be employed in other areas of the spinal column. For example, if the interbody device 10 is enlarged and shaped slightly differently, the device, system and method can be used in the lumbar and/or thoracic regions of the spine. The device, system and method can be used in vivo on human beings but can also be used for teaching purposes in cadavers, and plastic or other model spinal columns. In addition, the device, system and method can be used in veterinarian practices for invertebrate animals.

It should be noted that any specific feature from any or each of the disclosed or contemplated embodiments can be used in conjunction with or swapped with like features of other embodiments. For example, the screw threads 18s located on projection 18 can be added or removed from any of the embodiments. In addition, the specific geometrical shape for various structures, including the surfaces 11a-11f, knurls 16, and keel or projection(s) 18, 18a can be interchanged between any of the embodiments.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. A spinal interbody device, comprising:
   an interbody device configured to be placed between adjacent vertebrae of a spinal column, the interbody device including,
   an anterior surface,
   a posterior surface substantially opposed to the anterior surface,
   a lateral surface extending from the anterior surface to the posterior surface,
   a medial surface opposed to the lateral surface and extending from the anterior surface to the posterior surface,
   a superior surface connected to each of the anterior surface, posterior surface, lateral surface, and medial surface,
   an inferior surface opposed to the upper surface and connected to each of the anterior surface, posterior surface, lateral surface, and medial surface,
   an opening extending from the superior surface through the inferior surface, and at least one projection extending from at least one of the superior surface and inferior surface of the interbody device, the at least one projection including a self cutting structure, and the at least one projection configured to prevent movement of the interbody device relative to the adjacent vertebrae when implanted, wherein the self cutting structure includes a first face and a second face and a blade defined by the first face and the second face, a back surface formed opposite to the blade, the blade facing in a direction of implantation of the interbody device, and
   a ledge surface formed in front of the first face and the second face and opposite to the back surface,
   wherein the first face and the second face ramp upwardly from the ledge surface to form the blade.

2. The spinal interbody device of claim 1, wherein the outermost periphery of the superior surface is shaped as a trapezoid.

3. The spinal interbody device of claim 1, wherein the at least one projection is a spike located adjacent the opening and extending from the superior surface.

4. The spinal interbody device of claim 3, wherein spike is an integral and continuous portion of the interbody device.

5. The spinal interbody device of claim 3, wherein the at least one projection includes two spikes located on the superior surface of the interbody device and two spikes located on the inferior surface of the interbody device.

6. The spinal interbody device of claim 3, wherein the at least one projection includes two spikes located on the superior surface and closer to the posterior surface than to the anterior surface of the interbody device.

7. The spinal interbody device of claim 3, wherein the at least one projection includes two spikes located between the posterior surface and the opening in the interbody device.

8. The spinal interbody device of claim 1, wherein the superior surface includes a plurality of knurls.

9. The spinal interbody device of claim 1, wherein the at least one projection comprises a first spike and a second spike, the second spike having a different shape than the first spike.

10. The spinal interbody device of claim 1, wherein the blade separates the first face from the second face.

11. The spinal interbody device of claim 10, wherein at least one of the first face and the second face includes a concave surface.

12. The spinal interbody device of claim 10, wherein the at least one projection is formed as a spike that includes a first face and second face that define a blade therebetween, and a third face opposed to the blade.

13. The spinal interbody device of claim 1, further comprising:
    a secondary interbody device configured to be located adjacent the interbody device.

14. The spinal interbody device of claim 1, further comprising an insertion structure located on at least one of the anterior surface, the medial surface, and the lateral surface.

15. The spinal interbody device of claim 1, wherein at least one of the superior surface and inferior surface includes a surface texture that has a plurality of knurls.

16. The spinal interbody device of claim 1, wherein the interbody device is coated with a porous titanium coating.

17. The spinal interbody device of claim 1, wherein the self cutting structure includes a back surface opposing the blade and wherein the back surface is one of a rounded surface and a flat surface.

18. A spinal interbody device, comprising:
    an interbody device configured to be placed between adjacent vertebrae of a spinal column, the interbody device including,
    an anterior surface,
    a posterior surface substantially opposed to the anterior surface,
    a lateral surface extending from the anterior surface to the posterior surface,
    a medial surface opposed to the lateral surface and extending from the anterior surface to the posterior surface,
    a superior surface connected to each of the anterior surface, posterior surface, lateral surface, and medial surface, an inferior surface opposed to the upper surface and connected to each of the anterior surface, posterior surface, lateral surface, and medial surface, an opening extending from the superior surface through the inferior surface, and at least one projection extending from at least one of the superior surface and inferior surface of the interbody device, the at least one projection including a self cutting structure, and the at least one projection configured to prevent movement of the interbody device relative to the adjacent vertebrae when implanted, and a ledge surface formed flush with at least one of the superior surface and the inferior surface, wherein a blade extends from the ledge surface to a point of the at least one projection, and wherein the at least one projection includes a connection structure configured to permit removal of the at least one projection from at least one of the superior surface and the inferior surface, and wherein the interbody device includes a first aperture extending from the anterior surface to the superior surface and is configured for use with a first interbody device bone screw, and a second aperture extending from the anterior surface to the inferior surface and is configured for use with a second interbody device bone screw, and wherein the opening extends from the superior surface through the inferior surface along a central opening axis, and the interbody device first aperture has a first aperture central axis that forms an acute angle with the central opening axis, and the interbody device second aperture has a second aperture central axis that forms an acute angle with the central opening axis in the interbody device, and wherein the first aperture central axis forms an acute angle with respect to second aperture central axis.

19. The spinal interbody device of claim 18, wherein the at least one projection includes a back surface having one of a rounded shape and a flat shape.

20. The spinal interbody device of claim 18, wherein threads are configured to mate with threads located in the interbody device.

21. A spinal interbody system, comprising:
an interbody device configured to be placed between adjacent vertebrae of a spinal column, the interbody device including,
an anterior surface,
a posterior surface substantially opposed to the anterior surface,
a lateral surface extending from the anterior surface to the posterior surface,
a medial surface opposed to the lateral surface and extending from the anterior surface to the posterior surface,
a superior surface connected to each of the anterior surface, posterior surface, lateral surface, and medial surface,
an inferior surface opposed to the upper surface and connected to each of the anterior surface, posterior surface, lateral surface, and medial surface, and
an opening located at a central portion of the interbody device; and
at least one keel having a longitudinal axis and a superior end located at one end of the longitudinal axis and an inferior end located at an opposite end of the longitudinal axis, and the keel extending from the superior surface through the inferior surface, such that the superior end extends out from the superior surface of the interbody device, and the inferior end extends out from the inferior surface of the interbody device, wherein at least one of the superior end and the inferior end of the at least one keel includes a blade, the blade facing in a direction of implantation of the interbody device, and
a ledge surface formed flush with at least one of the superior surface and the inferior surface,
wherein the blade extends from the ledge surface to a point of the at least one keel.

22. The spinal interbody system of claim 21 wherein the blade faces away from the central portion of the interbody device.

23. The spinal interbody system of claim 21 wherein the blade is defined by a first face and second face each facing away from the opening in the interbody device to form a self cutting edge, the blade is configured such that during implantation of the interbody device the blade cuts through a portion of spinal tissue to arrive at a final implant location.

24. The spinal interbody system of claim 23 wherein the first face of the blade is concave and the second face of the blade is concave.

25. The spinal interbody system of claim 23 wherein the first face of the blade is one of concave and planar, and the second face of the blade is one of concave and planar.

26. The spinal interbody system of claim 21, further comprising:
a second keel having a second keel longitudinal axis, the second keel extending out from the superior surface and out from the inferior surface of the interbody device.

27. The spinal interbody system of claim 26, wherein the longitudinal axis of the at least one keel is substantially parallel with the longitudinal axis of the second keel.

28. The spinal interbody system of claim 26, wherein the second keel includes a second blade extending along the longitudinal axis of the second keel and facing away from the central portion of the interbody device.

29. The spinal interbody system of claim 21, wherein the inferior end and superior end of the at least one keel are each formed as a pointed spike.

30. The spinal interbody system of claim 29, wherein the blade extends from at least one of the pointed spike at the inferior end and the pointed spike at the superior end, the blade also extending along and located within a plane that contains the longitudinal axis of the at least one keel.

31. The spinal interbody system of claim 21, wherein the interbody device is coated with a porous titanium coating.

32. The spinal interbody device of claim 21, wherein the self cutting structure includes a back surface opposing the blade and wherein the back surface is one of a rounded surface and a flat surface.

* * * * *